United States Patent [19]

Schneider

[11] Patent Number: Plant 7,146

[45] Date of Patent: Feb. 13, 1990

[54] APPLE TREE — SCHNEICA

[76] Inventor: Georg Schneider, Grenzhofer Strasse 60, D-6803 Edingen-Neckarhausen 1, Fed. Rep. of Germany

[21] Appl. No.: 184,481

[22] Filed: Apr. 21, 1988

[51] Int. Cl.[4] ..... A01H 5/00

[52] U.S. Cl. ..... Plt./34

[58] Field of Search ..... Plt. 34

[56] References Cited

U.S. PATENT DOCUMENTS

P.P. 5,937 10/1984 Coster ..... Plt. 34

P.P. 6,148 4/1988 Ligonniere ..... Plt. 34

OTHER PUBLICATIONS

Brooks, Reid M., et al., *Register of New Fruit and Nut Varieties,* (2nd Ed), University of California Press, 1972, pp. 48–49.

*Primary Examiner*—James R. Feyrer

*Attorney, Agent, or Firm*—Webb, Burden, Ziesenheim & Webb

[57] ABSTRACT

'Schneica' is a sport of 'Jonagold' having a deeper overcolor intensity and flatter fruit shape, as well as a deeper eye than that of the fruit of the parent. Fruit is less long, lighter and less extensive in coloration, and later to color than that of 'Jonagored' which is a solid red, earlier to color and more acid tasting apple.

6 Drawing Sheets

BACKGROUND OF THE PLANT

This discovery relates to a new and distinct variety of apple tree identified by the varietal name Schneica. The new variety, which is a blossom bud to limb mutation of a Jonagold, was discovered in the discoverer's orchard in Edingen-Neckarhausen, Federal Republic of Germany, in the year 1980. The new variety appeared as a branch having a distinctive fruit on a Jonagold tree among a planting of young Jonagold trees. The new fruit of the variety exhibits a deeper overcolor intensity as compared with the Jonagold variety fruit, yet with a red hue faded in comparison. Also, the fruit is flatter and the eye end is deeper than the Jonagold fruit.

The tree having the new variety on its branch, and its fruit, were carefully observed and protected. During the course of the following year, the same overcolor intensity, faded hue and distinctive shape were observed on the apple fruit of the same branch. The rest of the tree showed no variation.

The discoverer obtained several scions from this branch and grated them onto several other trees. All of these graftings produced fruit with the same deep overcolor intensity, faded hue and distinctive shape. The procedure was repeated and there are now sixth generation trees bearing fruit. All grafts remain stable and no retrogression or degeneration has been observed.

DESCRIPTION OF THE DRAWINGS

The accompanying photographic drawings illustrate the new variety, with color being as nearly true as is possible with color illustrations of this type. The photographs of the apple tree were taken in the summer with natural light whereas the individual apple photographs were taken during the winter from stored apples using flash light.

DESCRIPTION OF THE PLANT

Figure 1:
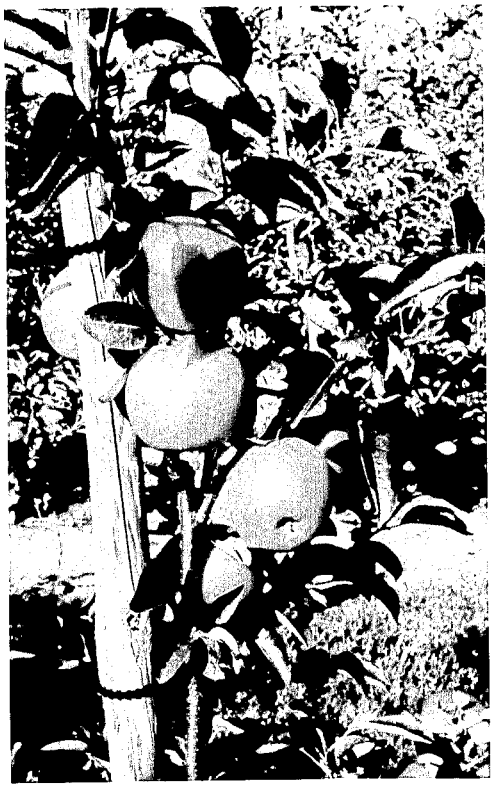
FIG. 1 is a photograph of the apple tree Schneica as described herein.
Figure 2:
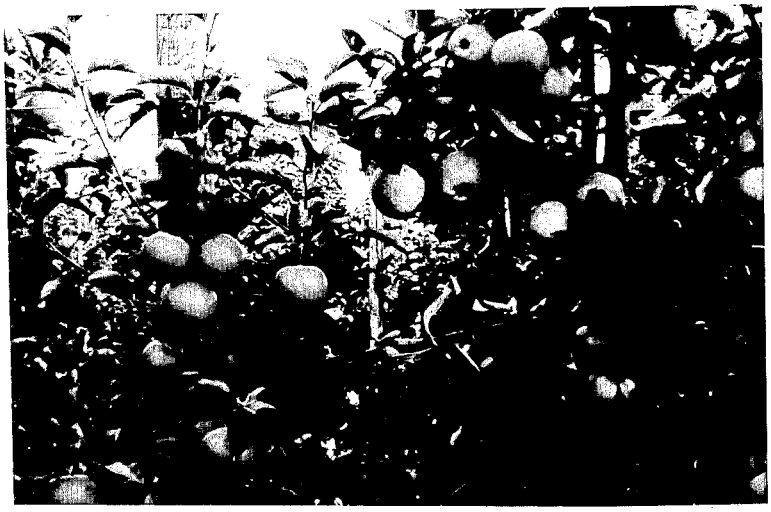
FIG. 2 is a photograph of the mother tree showing the more solid red apples of Schneica and the red/yellow apples of Jonagold.
Figure 3:
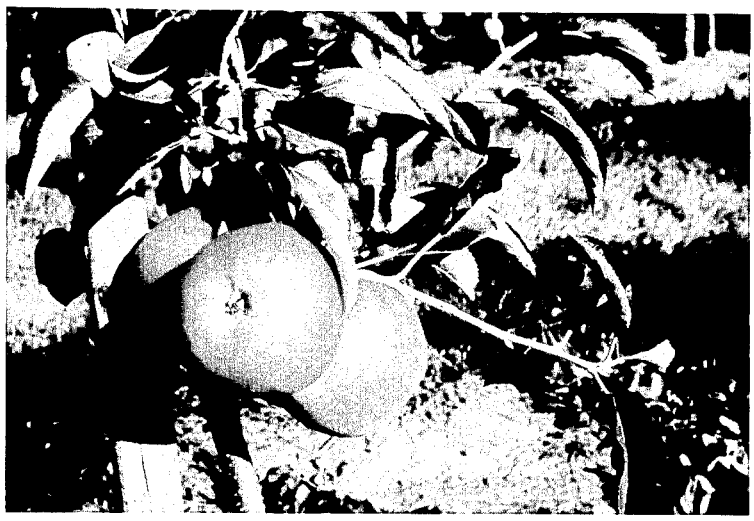
FIG. 3 is a photograph of a close-up of a clump of the Schneica apples.
Figure 4:
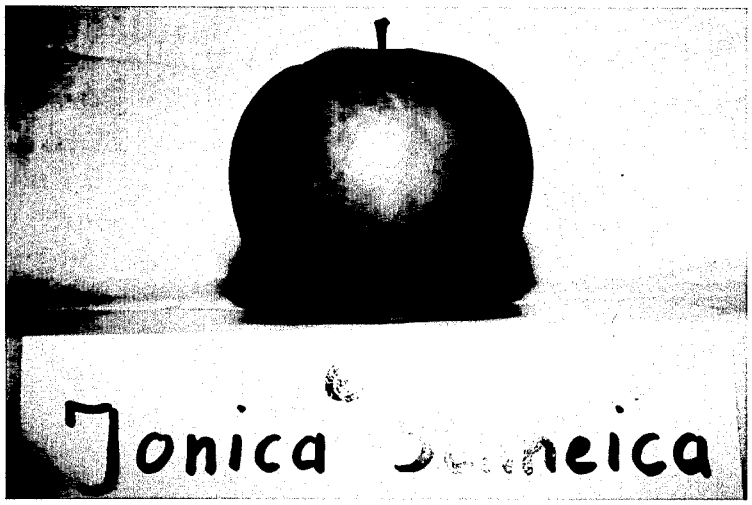
FIGS. 4–6 are photographs of the Schneica apple at different perspectives.
Figure 5:
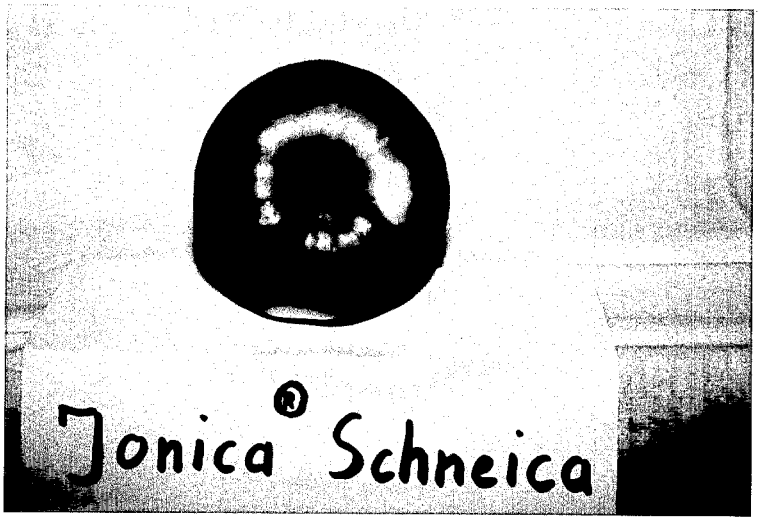
Figure 6:
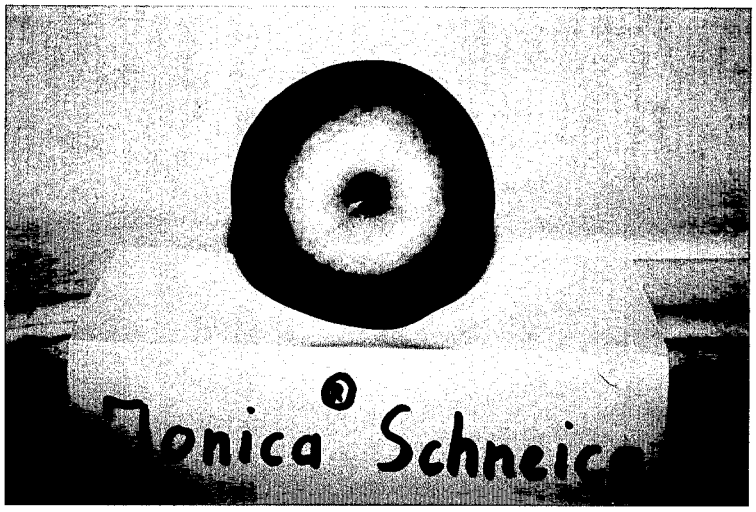
Figure 7:
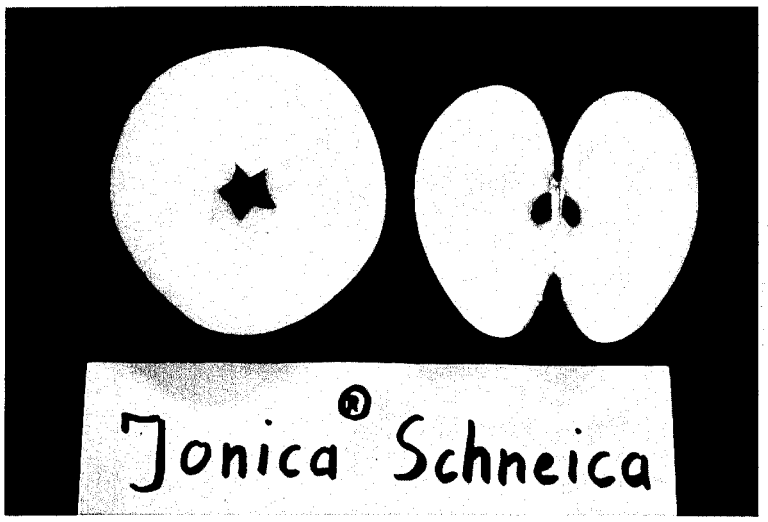
FIG. 7 is a photograph showing two Schneica apple halves taken on different planes.
Figure 8:
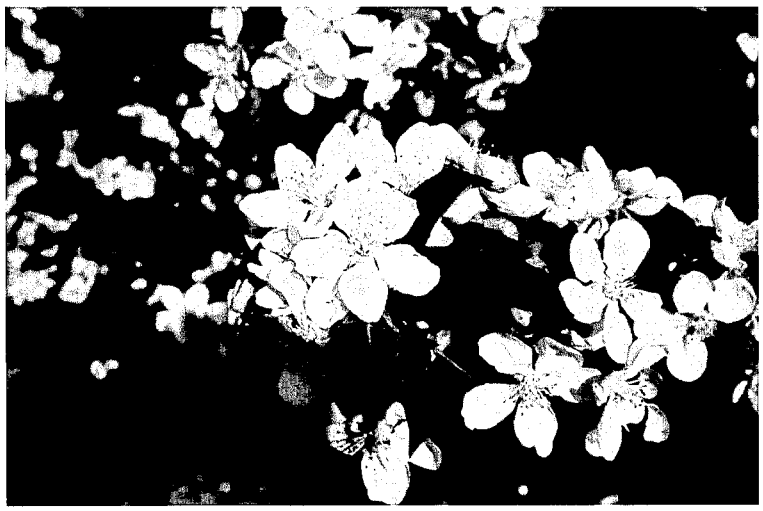
FIG. 8 is a photograph of the flowers of the Schneica tree.
Figure 9:
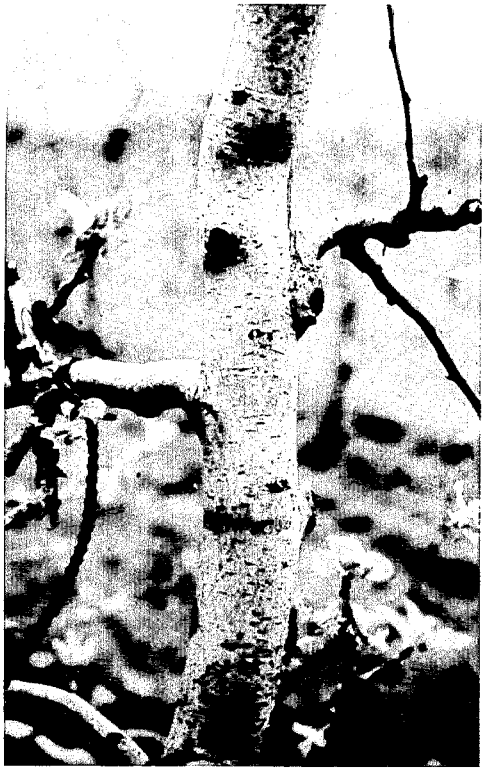
FIG. 9 is a photograph of the trunk of the Schneica tree.
Figure 10:
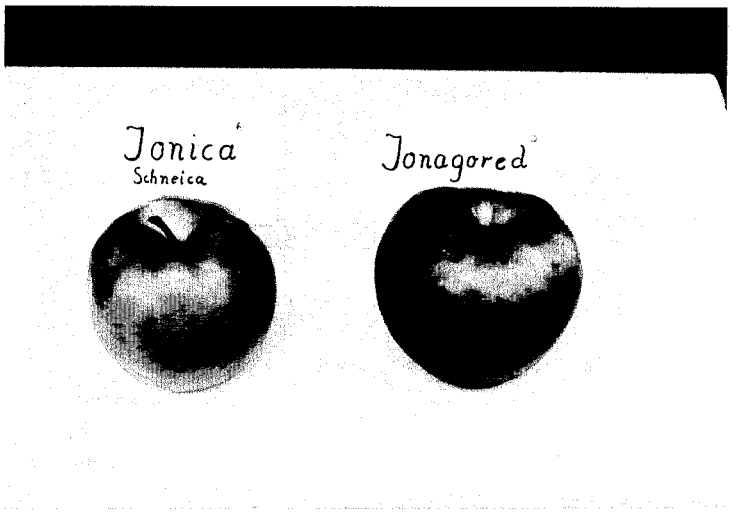
FIGS. 10 and 11 are comparisons at different perspectives and show the differences in color of Schneica apple and the Jonagored apple, which is another sport mutation of Jonagold and is described in U.S. Plant Pat. No. 5,937.
Figure 11:
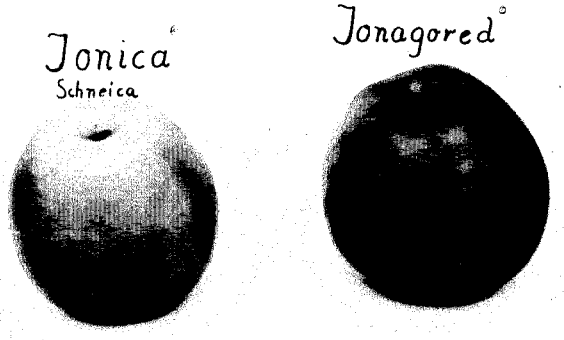

This new variety has all the known and favorable qualities of the Jonagold variety, such as medium sweetness and acidity, mid-season maturity, weak distinctness of core in section, and good production and storage characteristics. As an additional characteristic, however, this new variety shows as a major feature the deeper overcolor intensity identified above, which improves the optical impression and attractiveness of the fruit and substantially enhances its commercial value.

The specimens described were grown at Edingen-Neckarhausen, Federal Republic of Germany. The color descriptions which follow refer to Pflanzenfarbenatlas mit Farbtafel mit Farbzeichen nach DIN 6164 (German industry standard) mit der Genauigkeitsstufe ½ nach Prof. Dr. E. Biesalski. Corresponding *Royal Horticultural Society* (*R.H.S.*) *Colour Chart* values accompany the German Industry standard values.

Schneica and Jonagold bloom at the same time and have the same floral characteristics. Each develop their color in Edingen-Neckarhausen, Federal Republic of Germany at the end of September and are ripe for picking in October. The fruit size is substantially the same for both varieties. Other than the specific differences set forth hereinabove, the two varieties are virtually identical. Schneica may also be compared with Jonagored.

The fruit of Schneica is less oblong than that of Jonagored. Schneica is a lighter red than Jonagored which is all red and not blushed as in Schneica. Schneica develops its color 4 to 6 weeks after Jonagored. Schneica is less acidic to the taste than is Jonagored.

Tree: Medium size; medium vigor; relatively hardy and powerful with wide and low spreading; easy to trim; resistant to fungus and disease.

Trunk: Medium; smooth.

Branches: Medium thick; smooth; much branching. Lenticels: average number, medium large.

Leaves: Length, 4 inches (10 cm); Width, approximately 3 inches (7 cm); strong, medium thick, pronounced ribs; dark green.

Flowers: Full bloom (in West Germany), medium late; Size, large; Color, at the beginning of blooming, pink; Color, at peak of blooming, white with a very light pink blush on the reverse side.

Fruit:

*Shape.*—Length of axis, 2.6 inches (65 mm) average height, 2.8 inches (70 mm); average breadth, 3.2 inches (80 mm); overall flat, nontapering shape; Cavity of the stem is broad and of medium depth.

*Stem.*—Medium long, fleshy.

*Skin.*—Smooth; medium dry. Ground color, Table No. 1, 5 Rock Madwort-yellow D 1,5:5, 5:1,5 corresponding to R.H.S. Yellow-green group 153D. Overcolor, table No. 7.5 Avens Red, Fireglobe k 7, 5:5:3 corresponding to R.H.S. Red Group 47A covering about 75% of fruit at picking time.

*Core.*—Small, with seeds well developed.

*Flesh.*—Yellowish; juicy. Texture: Medium firm, moderately easily bruised; medium cells. Flavor: Rich; aromatic; pleasant relation between sugar and acidity. Quality: Best.

Seeds:

*Number perfect.*—10.

*Number in one cell.*—2.

*Length.*—0.32 inches (8 mm).

*Breadth.*—0.14 inches (3.5 mm).

*Color.*—Dark brown.

*Time of maturity.*—Early October.

*Maturity for consumption.*—Right after harvest up to July of following year, depending on kind of storage.

*Pollination.*—Partially self-pollinating, but a donator standing nearby is preferable.

I claim:

1. A new and distinct variety of apple tree named Schneica as described and illustrated, and particularly characterized by its relatively deep overcolor intensity.

* * * * *